United States Patent [19]

Matsui et al.

[11] Patent Number: 5,099,850
[45] Date of Patent: Mar. 31, 1992

[54] ULTRASONIC DIAGNOSTIC APPARATUS

[75] Inventors: Koichi Matsui, Tokyo; Yoshitake Saito, Kunitachi, both of Japan

[73] Assignee: Olympus Optical Co., Ltd., Tokyo, Japan

[21] Appl. No.: 464,212

[22] Filed: Jan. 12, 1990

[30] Foreign Application Priority Data

| Jan. 17, 1989 | [JP] | Japan | 1-5874 |
| Mar. 17, 1989 | [JP] | Japan | 1-63970 |
| Apr. 27, 1989 | [JP] | Japan | 1-108031 |
| Oct. 20, 1989 | [JP] | Japan | 1-273214 |
| Oct. 20, 1989 | [JP] | Japan | 1-273215 |
| Oct. 20, 1989 | [JP] | Japan | 1-273442 |

[51] Int. Cl.[5] ............................................. A61B 8/12
[52] U.S. Cl. .................................. 128/662.06; 128/4
[58] Field of Search ............... 128/660.01, 662.06, 128/660.09, 660.1, 653, 4

[56] References Cited

U.S. PATENT DOCUMENTS

| 3,817,089 | 6/1974 | Eggleton et al. | 128/662.06 |
| 4,391,282 | 7/1983 | Ando et al. | 128/662.06 |
| 4,605,009 | 8/1986 | Pourcelot et al. | 128/662.06 |
| 4,661,810 | 4/1987 | Himelstein et al. | 340/709 |
| 4,869,256 | 9/1989 | Kanno et al. | 128/662.06 X |
| 4,880,011 | 11/1989 | Imade et al. | 128/662.06 |

FOREIGN PATENT DOCUMENTS

| 3813298 | 11/1988 | Fed. Rep. of Germany . |
| 54-21760 | 2/1979 | Japan . |
| 58-83946 | 5/1983 | Japan . |
| 61-40073 | 9/1986 | Japan . |
| 63-115546 | 5/1988 | Japan . |

OTHER PUBLICATIONS

Meyer et al., "High Resolution Intreavascular Imaging via Ultrasonic Catheters: Proof of Concept", Proceedings of the IEEE, vol. 76, No. 9, pp. 1074–1078, Sep. 1988.

Primary Examiner—Francis Jaworski
Attorney, Agent, or Firm—Stevens, Davis, Miller & Mosher

[57] ABSTRACT

An ultrasonic diagnosing apparatus having an ultrasonic observation system for observing an ultrasonic tomographic image of a portion of a body of patient and an optical observation system for observing an optical image of the portion, a direction indicator is superimposed on an ultrasonic tomographic image displayed on a monitor screen, and the direction indicator is rotated on the monitor screen in accordance with the rotation of the ultrasonic tomographic image. The ultrasonic diagnosing apparatus further has a system for compensating for a deviation between the ultrasonic tomographic image displayed on the monitor screen and the optical image due to a twist of a flexible shaft which is extended in an insertion section of the apparatus to rotate an ultrasonic vibrating element arranged in a distal end of the insertion section.

18 Claims, 18 Drawing Sheets

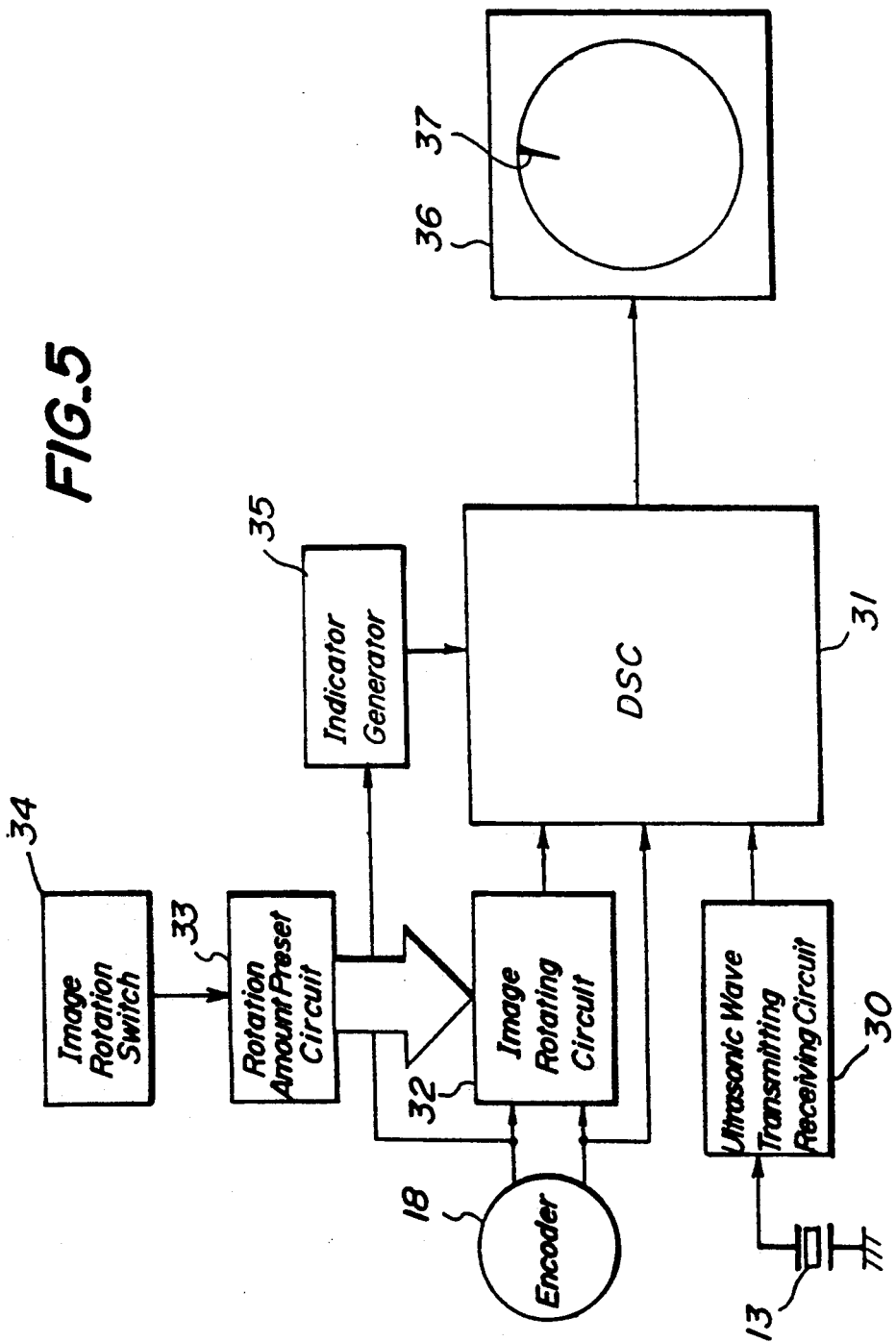

FIG.8A
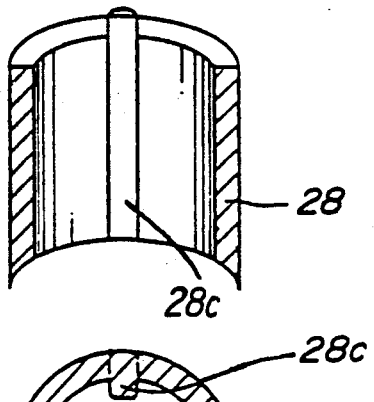
FIG.8B
FIG.9A
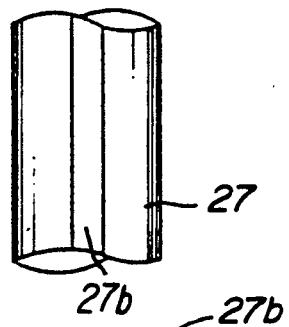
FIG.9B
FIG.10
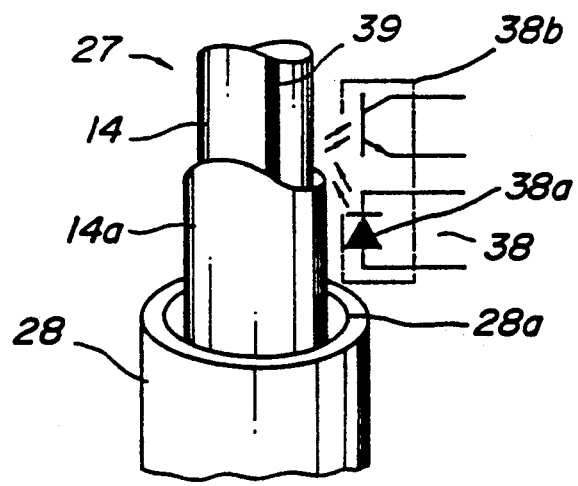

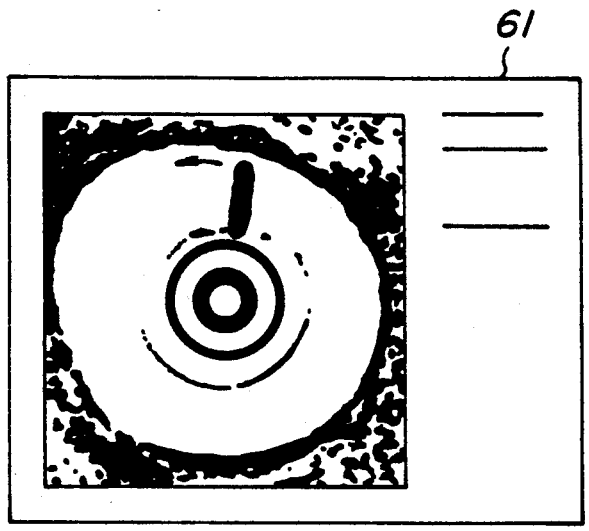
FIG._14A
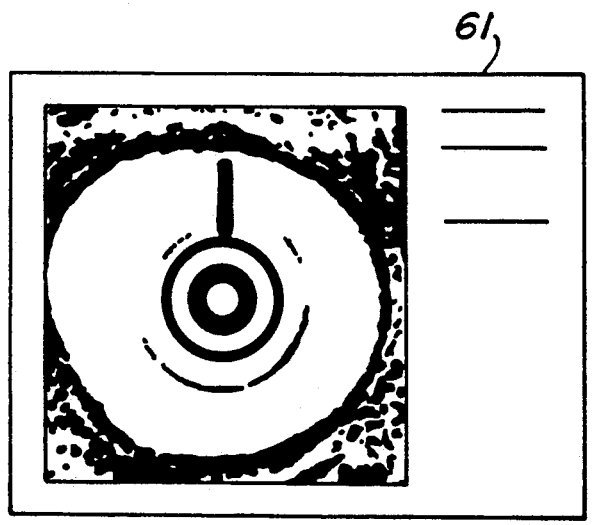
FIG._14B

ULTRASONIC DIAGNOSTIC APPARATUS

BACKGROUND OF THE INVENTION

Field of the Invention and Related Art Statement

The present invention relates to an ultrasonic diagnostic apparatus having an ultrasonic observation system to obtain an ultrasonic tomographic image of a portion of a body of patient with the aid of a ultrasonic waves and an optical observation system to obtain an optical image of the portion.

Such ultrasonic endoscope diagnostic apparatuses having the ultrasonic observation system and the optical observation system are widely used and disclosed in publications such as U.S. Pat. No. 4,605,009 and German Patent laid-open Publication No. 3336803. In the former publication, the apparatus is constructed such that an optical viewing field of the optical system and an ultrasonic observation field are made consistent with each other in a fixed manner, so that ultrasonic observation and optical observation can be effected simultaneously, while the positional relationship between the optical image and the ultrasonic tomographic image is maintained. In the later publication, the apparatus is constructed such that light exiting windows ar arranged in both sides of an ultrasonic vibrating element of linear scan type to make it possible for the endoscope arranged at the opposite side of the ultrasonic vibrating element to detect the light emitted from the windows, so that an operator can recognize the portion where the ultrasonic wave is emitted.

However, in these conventional ultrasonic endoscope diagnostic apparatus, it is sometimes difficult for the operator to recognize the positional relationship between the ultrasonic tomographic image and the optical image so that the operator cannot operate the endoscope in an effective manner. Particularly, in an ultrasonic endoscope diagnostic apparatus of radial scanning type, in order to obtain an ultrasonic tomographic image in a standard position, it is often required to rotate the ultrasonic tomographic image displayed on the monitor screen. When the ultrasonic tomographic image is rotated on the screen, the given positional relationship between the ultrasonic tomographic image and the optical image no longer exists so that it becomes difficult to recognize the direction of the optical image with respect to the ultrasonic tomographic image.

In Japanese Laid-open Patent Publication No. 60-227740 and Japanese Laid-open Utility Model Publication No. 61-57908, there are suggested known ultrasonic endoscope diagnostic apparatuses of radial scanning type. In these apparatuses, the ultrasonic vibrating element is rotatably arranged in the distal end portion of the insertion section of the apparatus and is connected to a distal end of a flexible shaft which is extended in the insertion section to transmit a rotation of a motor provided in the operating section of the apparatus to the ultrasonic vibrating element. In these apparatuses, a device for detecting the rotational position of the ultrasonic vibrating element arranged in the distal end portion of the insertion section of the apparatus is arranged in the operating section of the proximal end of the apparatus in order to make the insertion section small and short. However, when the insertion section is inserted in a cavity of a living body, the insertion section is bent along the curvature of the cavity. Further, in order to observe the desired portion of the cavity, the operator sometimes bend a bending section of the insertion section by operating angle knobs arranged in the operating section of the proximal end portion of the apparatus. In this case, a resistance against a rotational movement of the flexible shaft is increased and the flexible shaft becomes twisted, so that there would occur a deviation between the rotational phase of the ultrasonic vibrating element detected by a rotational phase detecting device such as an encoder and the actual rotational phase thereof. Therefore, the predetermined positional relationship between the ultrasonic tomographic image and the optical image would be altered.

In order to compensate for the deviation of the optical image with respect to the ultrasonic tomographic image, the insertion section is rotated in the cavity. However rotating the insertion section in the cavity is not undesirable not only because of the decrease in the durability of the insertion section but also because of the danger of transforation in the cavity.

On the other hand, an ultrasonic endoscope diagnostic apparatus having a miniature ultrasonic probe has been suggested. The apparatus is constructed such, that the miniature ultrasonic probe is capable of being inserted in a forceps channel which is provided in the insertion section of the apparatus, and the, distal end of the miniature ultrasonic probe is taken off from an opening arranged in the top end section of the insertion section to scan the portion of the body with the aid of ultrasonic waves. Such apparatus also has the same problem described above, so that, there would occur a deviation of the positional relationship between the ultrasonic tomographic image and the optical image.

SUMMARY OF THE INVENTION

The object of the present invention is to provide an ultrasonic diagnostic apparatus for observing an ultrasonic tomographic image of a portion within a body of a patient, in which a deviation of a predetermined positional relashionship between the ultrasonic tomographic image and the optical image can be compensated for in an effective manner.

It is another object of the invention to provide an ultrasonic diagnostic apparatus of radial scanning type in which even when the ultrasonic tomographic image is rotated on a monitor screen, wherein it is possible to make clear the predetermined positional relationship between the ultrasonic tomographic image and the optical image.

It is another object of the invention to provide an ultrasonic diagnostic apparatus, in which any deviation in the direction between the ultrasonic tomographic image and the optical image due to the twist of a flexible shaft for rotating the ultrasonic vibrating element can be corrected.

It is still another object of the invention to provide an ultrasonic diagnostic apparatus, in which said deviation in direction can be corrected automatically by detecting the amount and/or the direction of the twist of the flexible shaft.

According to the invention, an ultrasonic diagnostic apparatus for observing an ultrasonic tomographic image of a portion within a body of a patient comprises:

an insertion section which is insertable into a cavity of the body of the patient and having a distal end and a proximal end;

an optical observation means for observing an optical image of said portion of the body of the patient, said optical system means including an objective lens system arranged at the distal end of the insertion section and defining an observation field;

an ultrasonic observation means for observing an ultrasonic tomographic image of the portion within the body of the patient and having an ultrasonic vibrating element arranged within the distal end of the insertion section;

a display means electrically coupled with said ultrasonic vibrating element and having a display screen for displaying the ultrasonic tomographic image of the portion within the body of the patient; and a display controlling means for displaying a direction indicator in a superimposed manner with the ultrasonic tomographic image displayed on the display screen of the displaying means, said direction indicator representing a predetermined positional relationship between the ultrasonic tomographic image and the optical image.

According to another aspect of the invention, an ultrasonic diagnostic apparatus for observing an ultrasonic tomographic image of a portion within a body of a patient comprises:

an insertion section which is insertable into a cavity of the body of patient and having a distal end and a proximal end;

an optical observation means for observing an optical image of said portion of the body of the patient, said optical system means including an objective lens system arranged at the distal end of the insertion section and defining an observation field;

an ultrasonic observation means for observing an ultrasonic tomographic image of the portion within the body of the patient and having an ultrasonic vibrating element arranged within the distal end of the insertion section;

a display means electrically coupled with said ultrasonic vibrating element for receiving an echo signal generated from the ultrasonic vibrating element and displaying the ultrasonic tomographic image of the portion within the body of the patient on a display screen; and a display controlling means for rotating the ultrasonic tomographic image displayed on the display screen of the displaying means, whereby any deviation between the ultrasonic tomographic image and the optical image can be compensated for by rotating the ultrasonic tomographic image on the display screen.

According to a further aspect of the invention, an ultrasonic diagnostic apparatus for observing an ultrasonic tomographic image of a portion within a body of a patient comprises:

an insertion section which is insertable into a cavity of the body of patient and having a distal end, a proximal end and a bending section arranged near the distal end;

an ultrasonic observation means for observing an ultrasonic tomographic image of the portion within the body of the patient and having an ultrasonic vibrating element arranged within the distal end of the insertion section;

a display means electrically coupled with said ultrasonic vibrating element for receiving an echo signal supplied from the ultrasonic vibrating element to produce a video signal and displaying the ultrasonic tomographic image of the portion within the body of the patient on a display screen;

a twist detecting means for detecting an amount or an amount and a direction of the bending movement of the bending section of the insertion section to produce a twist detection signal; and a display controlling means for receiving the twist detection signal and rotating the ultrasonic tomographic image displayed on the display screen of the displaying means in accordance with the twist detection signal.

BRIEF DESCRIPTION OF THE DRAWINGS

FIG. 5 is a block diagram showing the construction of the first embodiment of the invention;

FIGS. 8A, 8B, 9A and 9B are cross sectional views illustrating a part of the insertion section of the apparatus according to the third embodiment of the invention;

FIG. 10 is a schematic view representing a part of the insertion section of the apparatus according to the fourth embodiment of the invention;

FIGS. 14A and 14B are schematic views depicting ultrasonic tomographic images displayed on the monitor screen;

DESCRIPTION OF THE PREFERRED EMBODIMENT

Figure 1:
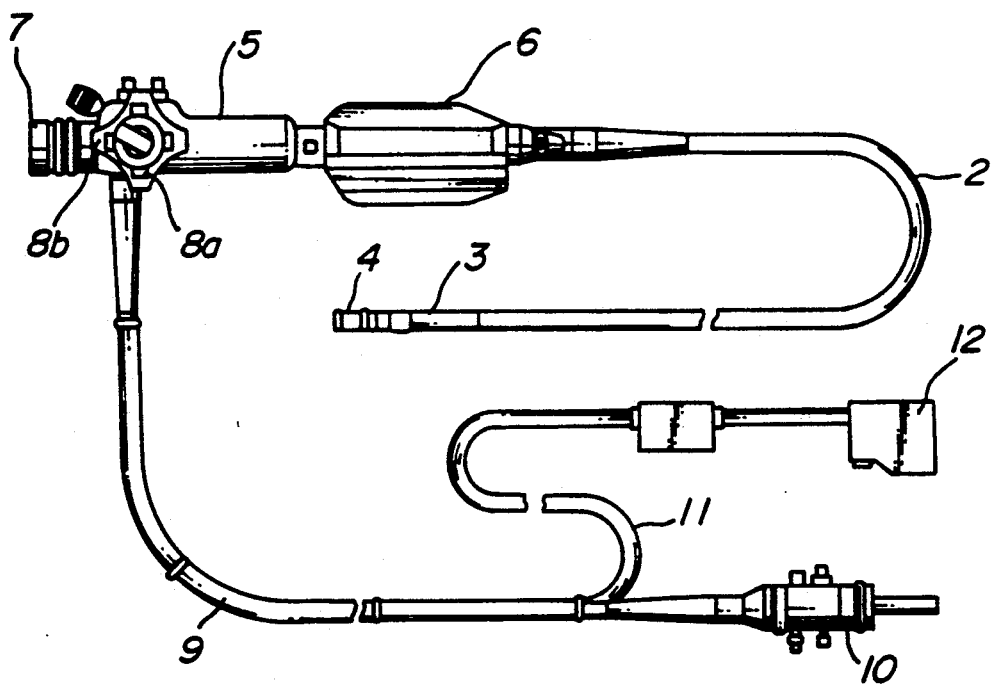
FIG. 1 is a schematic view showing a whole structure of the ultrasonic endoscope diagnostic apparatus according to the invention.

FIG. 1 is a schematic view showing the overall construction of an ultrasonic diagnostic apparatus according to the first embodiment of the present invention. In the present embodiment, the apparatus is constructed as an ultrasonic endoscope. In FIG. 1, the ultrasonic endoscope 1 comprises an insertion section 2, a bending section 3 and a top end section 4 provided at a distal end of the inserting section 2, a main operating section 5, and a sub operating section 6 provided at a proximal end of the insertion section 2, an eyepiece section 7 provided on the main operating section 5 and angle knobs 8a, 8b for bending the bending section 3 in the up and down and the right and left directions, respectively. From the main operating section 5, there is extended a universal cable 9 which is connectable to an optical observating device (not shown) via a connector 10. As will be explained later, in the top end section 4, is provided an ultrasonic vibrating element which is rotated by a motor arranged in the sub operating section 6 by means of a flexible shaft arranged within the insertion section 2. The ultrasonic vibrating element is electrically coupled with an ultrasonic observating device (not shown) via the universal cable 9, a cable 11 and a connector 12.

Figure 2:
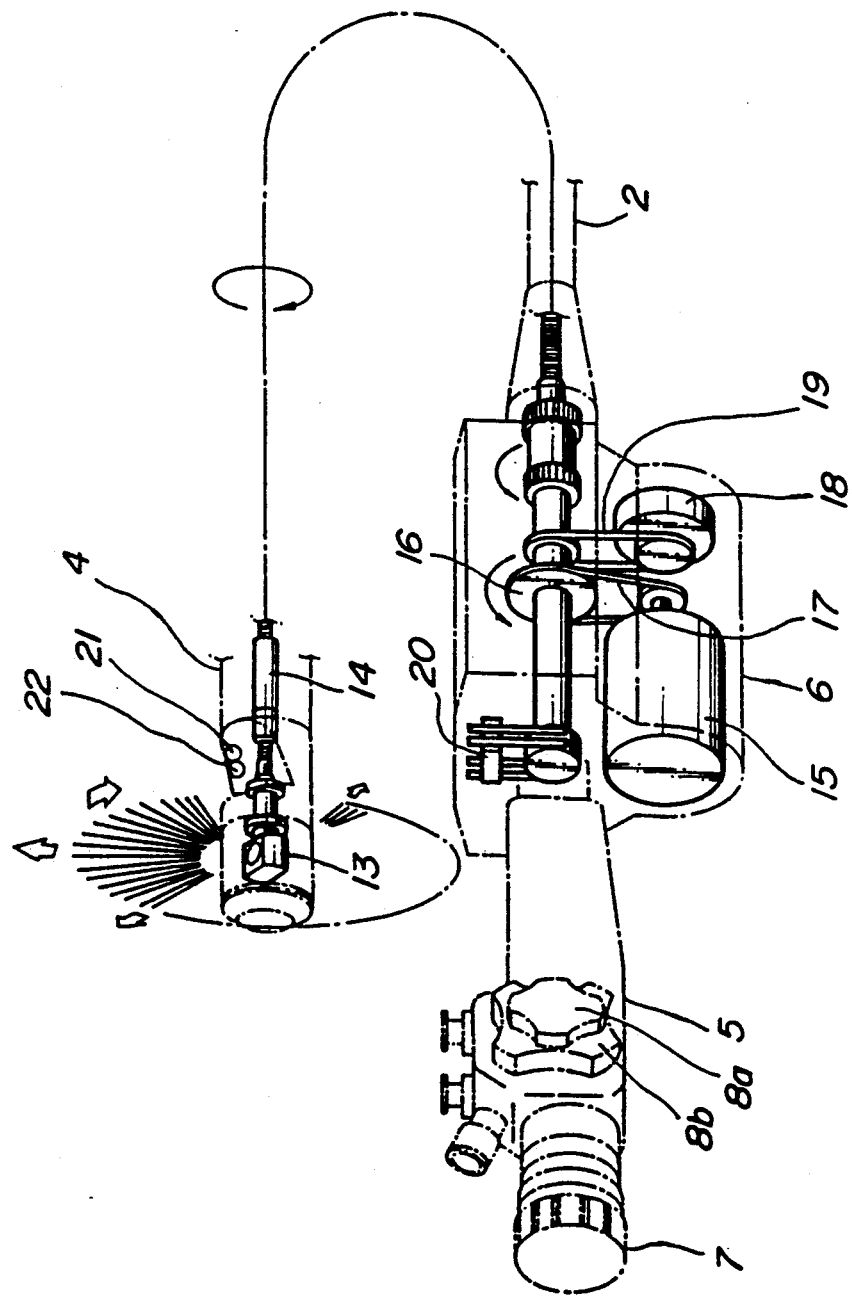
FIG. 2 is a schematic view depicting a structure of the ultrasonic endoscope diagnostic apparatus according to the first embodiment of the invention.

FIG. 2 is a schematic view depicting the top end section 4 and the main and sub operating sections 5 and 6. In the top end section 4 of the insertion section 2, there is rotatably arranged an ultrasonic vibrating element 13 which is coupled with a distal end of a flexible shaft 14. The flexible shaft 14 is extended in the insertion section 2 from the top end section 4 to the sub operating section 6 and the proximal end portion thereof is connected to a driving motor 15 via a pulley 16 and a belt 17, so that a rotation of the motor 15 is transmitted to the ultrasonic vibrating element 13 via the flexible shaft 14. Therefore, the ultrasonic vibrating element 13 is rotated in a radial direction of the insertion section 2 to effect the radial scanning.

To the proximal end portion of the flexible shaft 14, is further connected an encoder 18 via a belt 19 to detect the rotation of the ultrasonic vibrating element 13. A slip ring 20 is also provided on the shaft 14 to electrically couple the ultrasonic vibrating element 13 with the ultrasonic observating device. In the top end section 4, there are provided an illumination lens system 21 and an objective lens system 22 for effecting the optical observation of the portion of the body in an optical manner.

Figure 3:
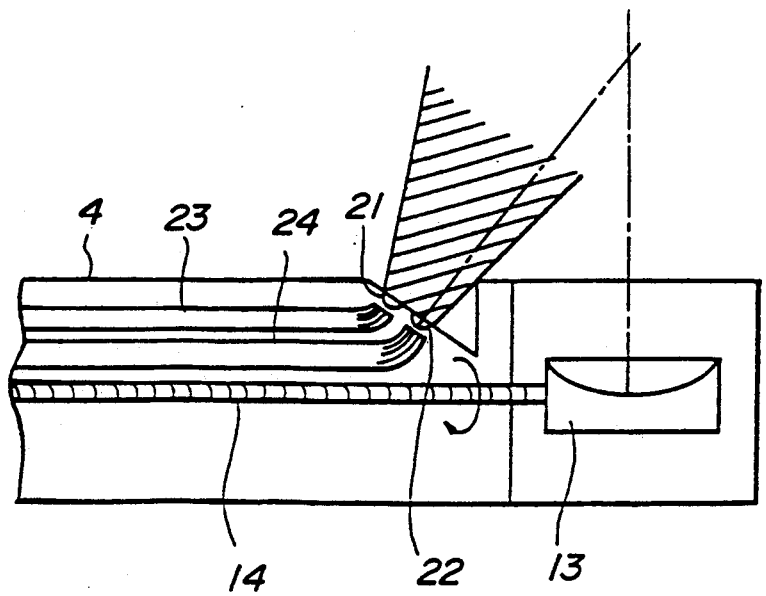
FIG. 3 is a schematic view illustrating a top end section of an insertion section of the apparatus according to the first embodiment of the invention.

FIG. 3 is a schematic view illustrating the top end section of the insertion section 2 according to the first embodiment of the invention. In the insertion section 2, there are extended a light guide 23 and an image guide 24 whose distal ends are arranged to face the illumination lens system 21 and the objective lens system 22, respectively. In the first embodiment, the rotational position of the ultrasonic vibrating element 13 when an ultrasonic wave emitted from the ultrasonic vibrating element 13 intersects with an optical axis of the objective lens system 22, is determined as a standard rotational position of the ultrasonic vibrating element 13.

Figure 4A:
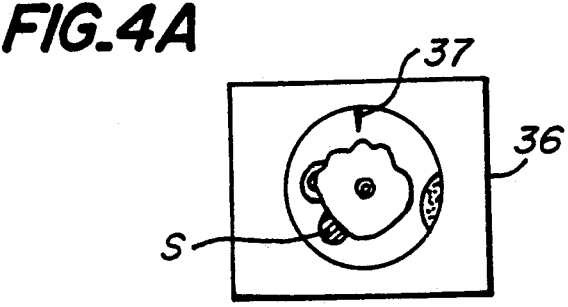
FIGS. 4A and 4B are schematic views representing ultrasonic tomographic images displayed on a monitor screen.
Figure 4B:
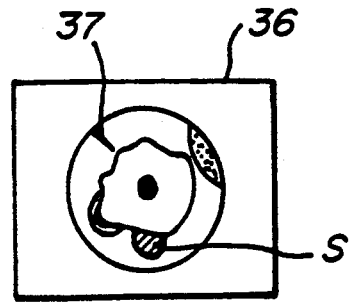

FIG. 4A shows a typical ultrasonic tomographic image displayed on a monitor screen 36. In case of effecting the diagnosis on the basis of the ultrasonic tomographic image, it is desired to display the image such that a known standard object S is displayed in a predetermined direction on the monitor screen. That is to say, in FIG. 4A the object S should be displayed in the downward direction. In the present embodiment, the ultrasonic tomographic image is rotated on the monitor screen by such an angle that the object S is displayed in the downward direction as shown in FIG. 4B. In this case, the predetermined positional relationship between the direction of the ultrasonic tomographic image and the direction of the optical image is changed so that the ultrasonic endoscope could not be handled easily.

FIG. 5 is a block diagram of the ultrasonic endoscope diagnostic apparatus according to the first embodiment of the invention. The ultrasonic vibrating element 13 is connected to an ultrasonic wave transmitting-receiving circuit 30. The circuit 30 is connected to a digital scan converter (DSC) 31 to supply an echo signal to the DSC 31.

The encoder 18 generates an origin signal and timing pulses. The origin signal is generated once during one revolution of the ultrasonic vibrating element 13 at such a timing that the element 13 generates an ultrasonic wave in the direction which intersects with the optical axis of the objective lens 22. The timing pulse is produced each time the ultrasonic vibrating element 13 is rotated by a predetermined angle such as 256/360 degrees. The timing pulses are directly supplied to the DSC 31 and the origin signal is supplied to an image rotating circuit 32 including a counter for counting the timing pulses supplied from the encoder 18. In order to rotate the ultrasonic tomographic image on the monitor screen to the image rotating circuit 32 is connected a rotation amount preset circuit 33 to which is connected an image rotation switch 34.

By operating the image rotation switch 34, the rotation amount preset circuit 33 produces a preset count corresponding to the rotation angle of the ultrasonic tomographic image. This preset count is supplied to the image rotating circuit 32. In response to the origin signal the counter in the image rotating circuit 32 begins to count the timing pulses supplied from the encoder 18. When the count value reaches the preset count, the image rotating circuit 32 generates a display start signal. This display start signal is supplied to the DSC 31. Then the DSC 31 starts to supply the video signal to the monitor 36 and the display of the ultrasonic tomographic image is started from the predetermined upper direction of the radial scanning. In this manner, the display signal is delayed by a time period corresponding to the rotation angle of the ultrasonic tomographic image. In order to compensate for the deviation between the ultrasonic tomographic image and the optical image, the origin signal is further supplied to an indicator generator 35 for generating a video signal of a direction indicator. The video signal thus generated is supplied to the DSC 31 and is superimposed on the ultrasonic tomographic image to display a direction indicator 37 on the display monitor 36. It should be noted that the direction indicator 37 is composed of several scanning lines. Since the display start signal is delayed with respect to the origin signal the direction indicator 37 is also rotated by the same angle as the rotation angle of the ultrasonical tomographic image as shown in FIG. 4B. In this manner, the operator can know the direction of the optical axis of the objective lens 22, i.e., the viewing direction of the optical image, even if the ultrasonic tomographic image is rotated by any desired angle.

Figure 6:
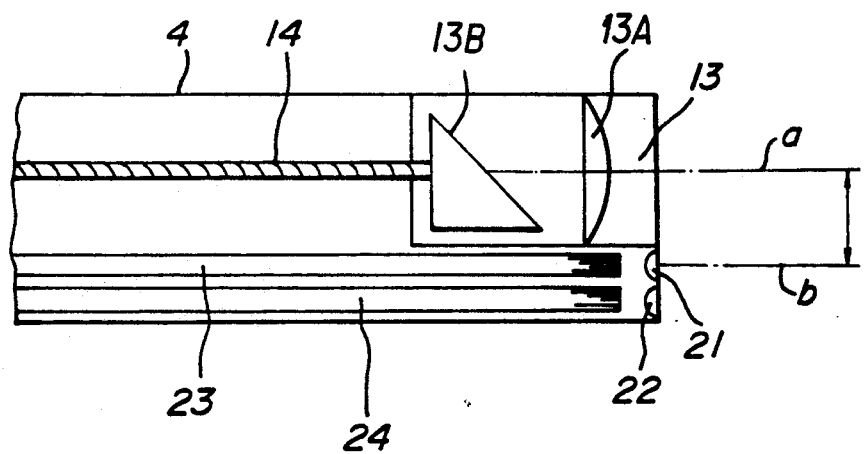
FIG. 6 is a schematic view showing a top end section of the insertion section of the apparatus according to the second embodiment of the invention.

FIG. 6 is a schematic view of the top end section 4 of the insertion section 2 of the apparatus according to the second embodiment of the invention. In the second embodiment, the illumination optical system 21 and the objective optical system 22 are arranged in a top end of the insertion section 2 to observe the portion of the cavity in a insertion direction of the insertion section 2. In the present embodiment, the ultrasonic vibrating element 13 comprises an ultrasonic vibrator 13A and a rotation mirror 13B. The ultrasonic vibrator 13A is arranged in a top end of the inserting section 2 and ultrasonic wave is emitted to the backward direction of the insertion section 2. At the backside portion of the ultrasonic vibrator 13A, is arranged the mirror 13B to reflect the ultrasonic wave emitted from the ultrasonic vibrator 13A as well as the echo wave reflected from the body. The mirror 13B is coupled with the distal end of the flexible shaft 14 to be rotated in a radial direction of the insertion section 2, so that radial scanning can be effected by reflecting the ultrasonic wave emitted from the ultrasonic vibrator 13A. The other structure of the apparatus is the same as that of the first embodiment. In the second embodiment, the rotational position of the mirror 13B when the ultrasonic scanning direction becomes parallel to a line connecting a rotational center axis a of the flexible shaft 14 and an optical axis b of the objective lens system 22 is determined as a standard rotational position. The rotational position of the mirror 13B is detected by the encoder 18 arranged in the sub-operating section 6. And at the timing that the encoder 18 detects the fact that the mirror 13B comes to the standard rotational position, the origin signal is produced by the encoder 18. Since the apparatus of the second embodiment has the same circuit construction as that of the first embodiment the direction indicator 37 indicating the optical axis of the objective lens system 22 is superimposed on the ultrasonic image displayed on the monitor screen 36.

Figure 7:
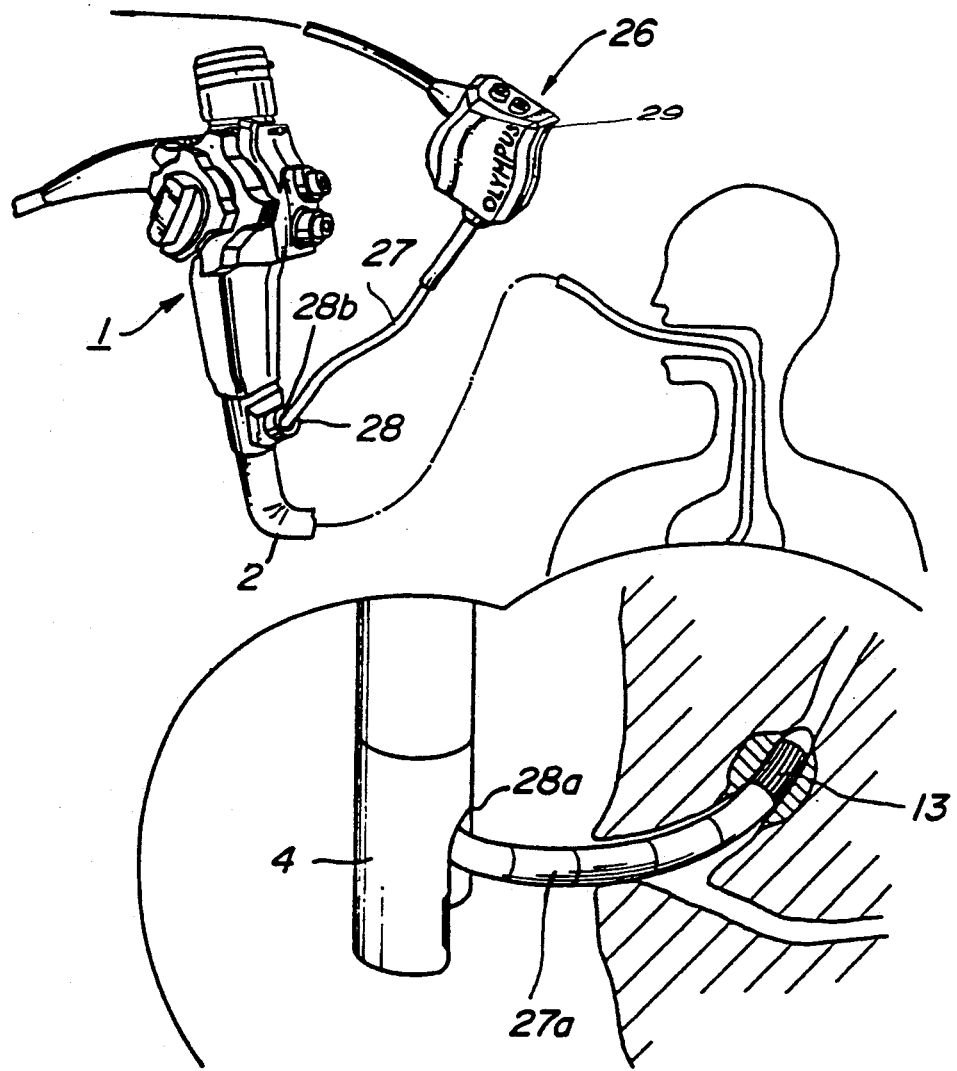
FIG. 7 is a schematic view depicting an apparatus having a miniature ultrasonic prove.

FIG. 7 is a schematic view representing an ultrasonic endoscope diagnostic apparatus having a miniature ultrasonic probe. In this apparatus, a miniature ultrasonic probe 26 is used such that an insertion tube 27 of the ultrasonic probe 26 is inserted within a channel 28 provided in the insertion section 2 of the apparatus and the distal top portion 27a of the insertion tube 27 is took off from an opening 28a of the channel 28 arranged in the top end section 4 of the insertion section 2 to scan the portion of the cavity with the aid of ultrasonic wave. An opening 28b for inserting the insertion tube 27 of the ultrasonic probe 26 is arranged in the proximal end portion of the insertion section 2. In the insertion tube 27 is provided the flexible shaft 14 which is connected to the ultrasonic vibrating element 13 to transmit the rotation of the driving motor 5 arranged in an ultrasonic operating section 29 to the ultrasonic vibrating element 13.

FIGS. 8A, 8B, 9A and 9A,9B schematic views showing a structure of the channel 28 and the insertion tube 27 of the apparatus, respectively, according to the third embodiment of the invention. As shown in FIGS. 8A and 8B in an inner side wall of the channel 28 is formed a convex portion 28c along the longitudinal direction of the channel 28. On the other hand, FIGS. 9A and 9B show that in an outer side wall of the insertion tube 27 is formed a concave portion 27b. In this embodiment, since the insertion tube 27 is not rotated in the channel 28 by coupling the convex portion 28c into the concave portion 27c, the predetermined standard rotational position of the ultrasonic vibrating element 13 with respect to the insertion section 2 can be kept constant.

Figure 11:
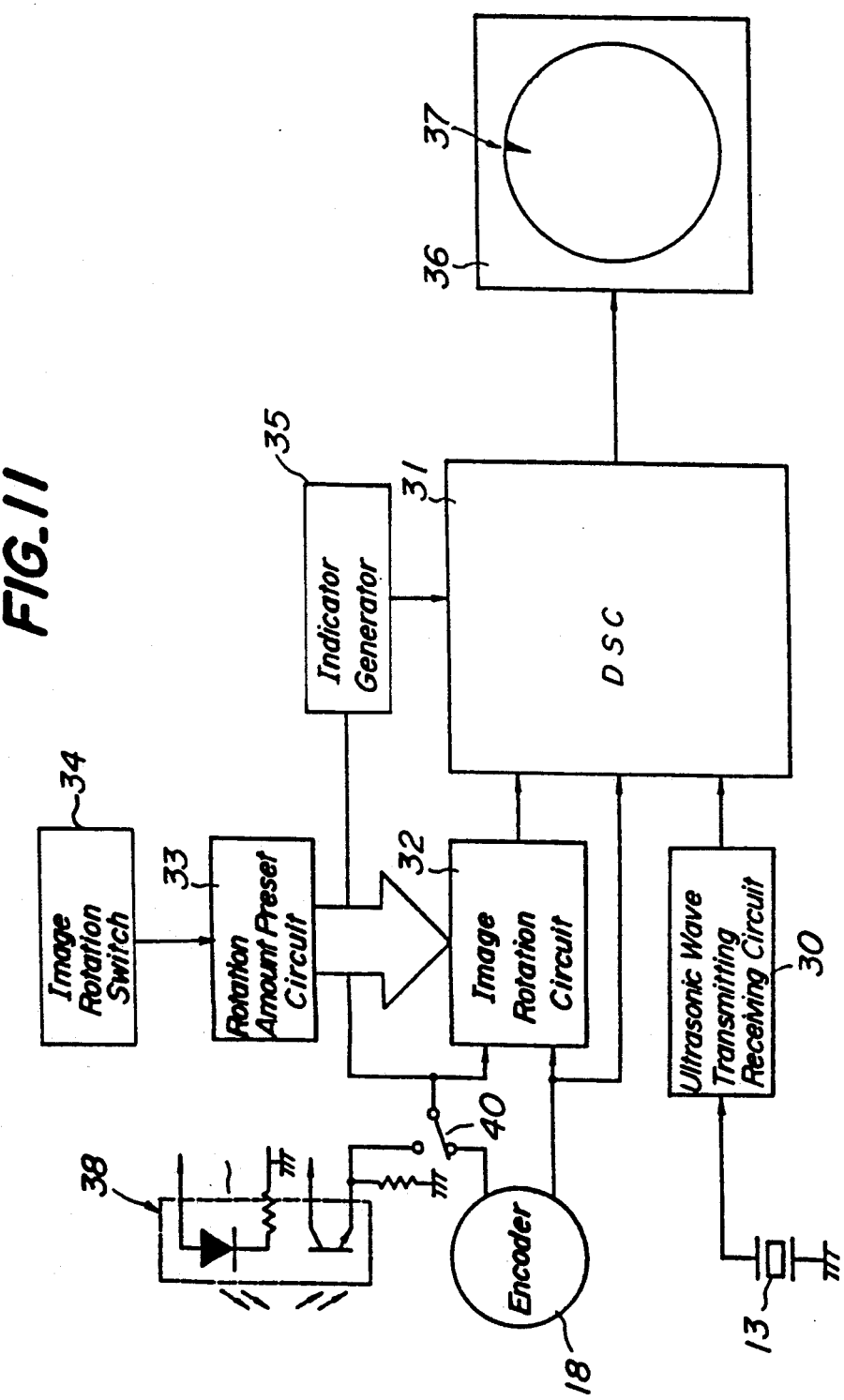
FIG. 11 is a block diagram illustrating the construction of the fourth embodiment of the invention.

FIG. 10, is a schematic view depicting the structure of the opening 28b of the channel 28 according to the fourth embodiment of the invention. As depicted in FIG. 10, in the vicinity of the opening 28b of the channel 28, there is provided a photo-sensor 38 comprising a light emitting diode 38a and a photo transistor 38b. The photo-sensor 38 detects a rotation of a mark 39, which is provided on the outer surface of the flexible shaft 14. via a transparent protection tube 14a. An rotation origin of the flexible shaft 14 with respect to the direction of the optical viewing field can be detected by detecting the mark 39 by the photosensor 38. A signal representing the rotation origin of the flexible shaft 14 is supplied to the image rotating circuit 32 via a switch 40 instead of the origin signal supplied from the encoder 18, as shown in FIG. 11. In case that only the ultrasonic probe is used, for example, for observing a blood tube, the switch 40 should be switched so as to connect the encoder 18 to the image rotating circuit 32. In this case it is not necessary to detect the rotation origin of the flexible shaft 14 with respect to the direction of the optical viewing field.

Figure 12:
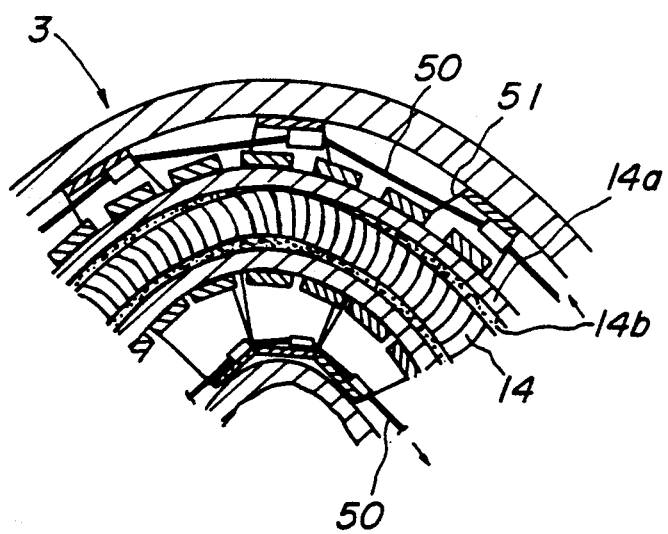
FIG. 12 is a schematic view showing an inside of the insertion section of the apparatus.

As explained in the preamble, when the bending section of the insertion section is bent by means of the angle knobs 8a, 8b, the resistance against the rotational movement of the flexible shaft 14 for rotating the ultrasonic vibrating element 13 is increased and the flexible shaft is twisted. As shown in FIG. 12, the flexible shaft 14 is inserted in a flexible tube 14a and a lubricating fluid 14b is filled in a space between the shaft 14 and the tube 14a. When, the bending section 3 is bent by moving an angle wire 50 coupled with junction pieces 51 as shown by arrows, the top outer wall of the flexible shaft is directly urged against the inner wall of the tube 14a so that there is produced a frictional resistance therebetween. When the flexible shaft 14 is twisted, the predetermined positional relationship between the ultrasonic tomographic image and the optical image is changed. In the following embodiments of the ultrasonic endoscope apparatus according to the invention, the deviation of the positional relationship can be corrected.

Figure 13:
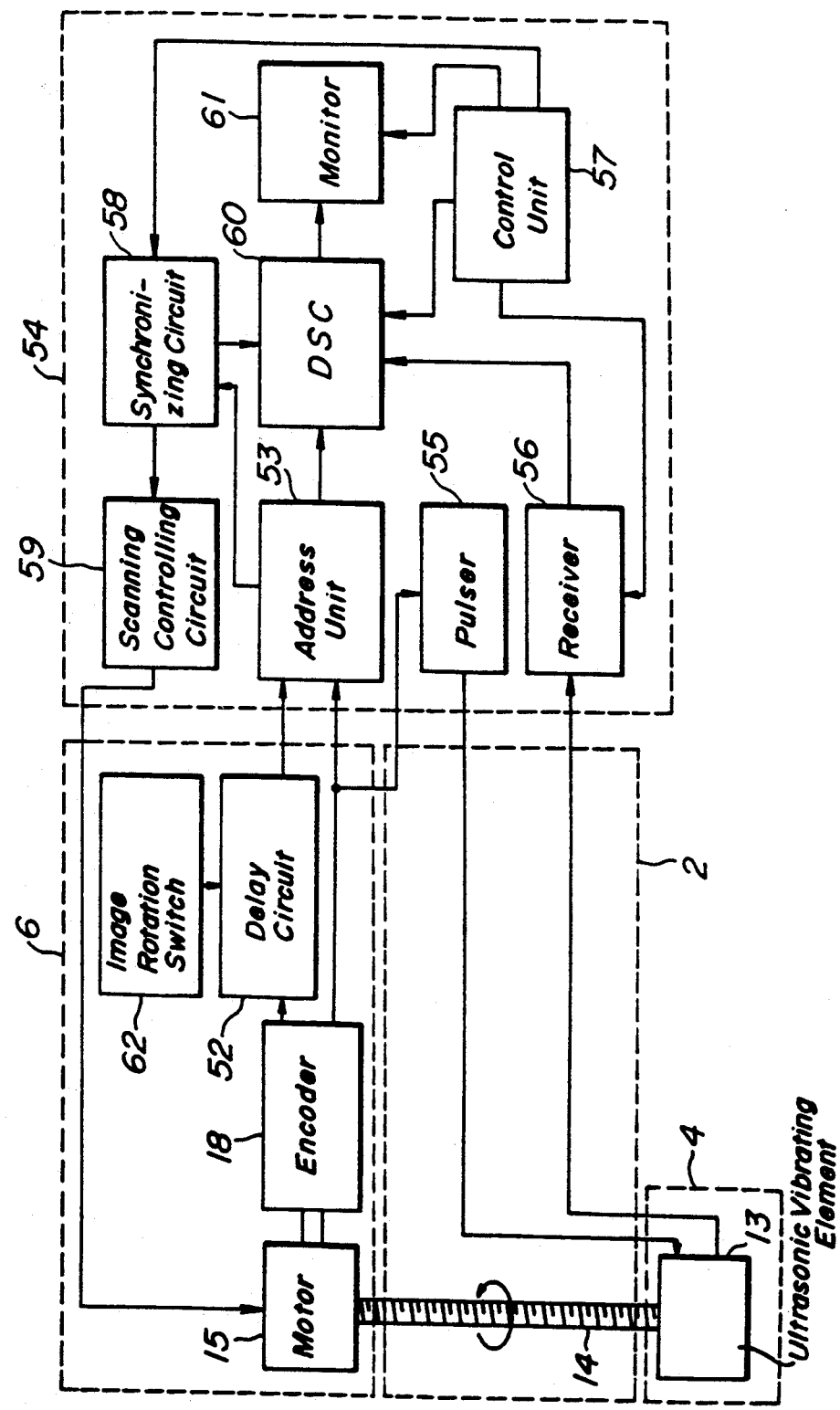
FIG. 13 is a block diagram depicting the construction of the fifth embodiment of the invention.

FIG. 13 is a block diagram showing a fifth embodiment of the ultrasonic endoscope apparatus according to the invention. In the present embodiment, portions similar to those shown in the previous embodiments are denoted by the same reference numerals. In this embodiment, the origin signal (Z phase signal) is supplied via a delay circuit 52 to an address unit 53 provided in an ultrasonic observating device 54. The timing pulses (A phase signal) generated from the encoder 18 are directly supplied to the address unit 5 as well as to a pulsar 55 which generates a transmission pulse in synchronism with the A phase signal, said transmission pulse being supplied to the ultrasonic vibrating element 13. Then the ultrasonic vibrating element 13 emits a pulsatory ultrasonic wave and receive an ultrasonic echo reflected from portions within the body of patient to generate an echo signal. The echo signal is received by a receiver 56 which is controlled by a control unit 57.

The control unit 57 also controls a synchronizing circuit 58 which controls a scanner controlling circuit 59 and a DSC 60 in a synchronizing manner. The scanner controlling circuit 59 produces a driving signal for the motor 15. Under the control of the control unit 57, the DSC 60 receives the echo signal from the receiver 56 and an address signal from the address unit 53 to generate a video signal. And the video signal is supplied to a monitor 61 to display the ultrasonic tomographic image thereon in the radial scanning mode. As explained above with reference to FIG. 12, the predetermined positional relationship between the optical image and the ultrasonic tomographic image displayed on the monitor 61 is deviated due to the twist of the flexible shaft 14. In order to correct this deviation, in the present embodiment, to the delay circuit 52 is connected a image rotation switch 62 which controls a delay time in the delay circuit 52. By operating the image rotation switch 62 provided on the sub-operating unit 6 with reference to the optical image and the ultrasonic tomographic image, it is possible to change the delay time by which the Z phase signal is delayed in the delay circuit 52. Since the Z phase signal is used as the display start signal, the ultrasonic tomographic image can be rotated on the monitor 61 as shown in FIGS. 14A and 14B, by delaying the Z phase signal.

Figure 15:
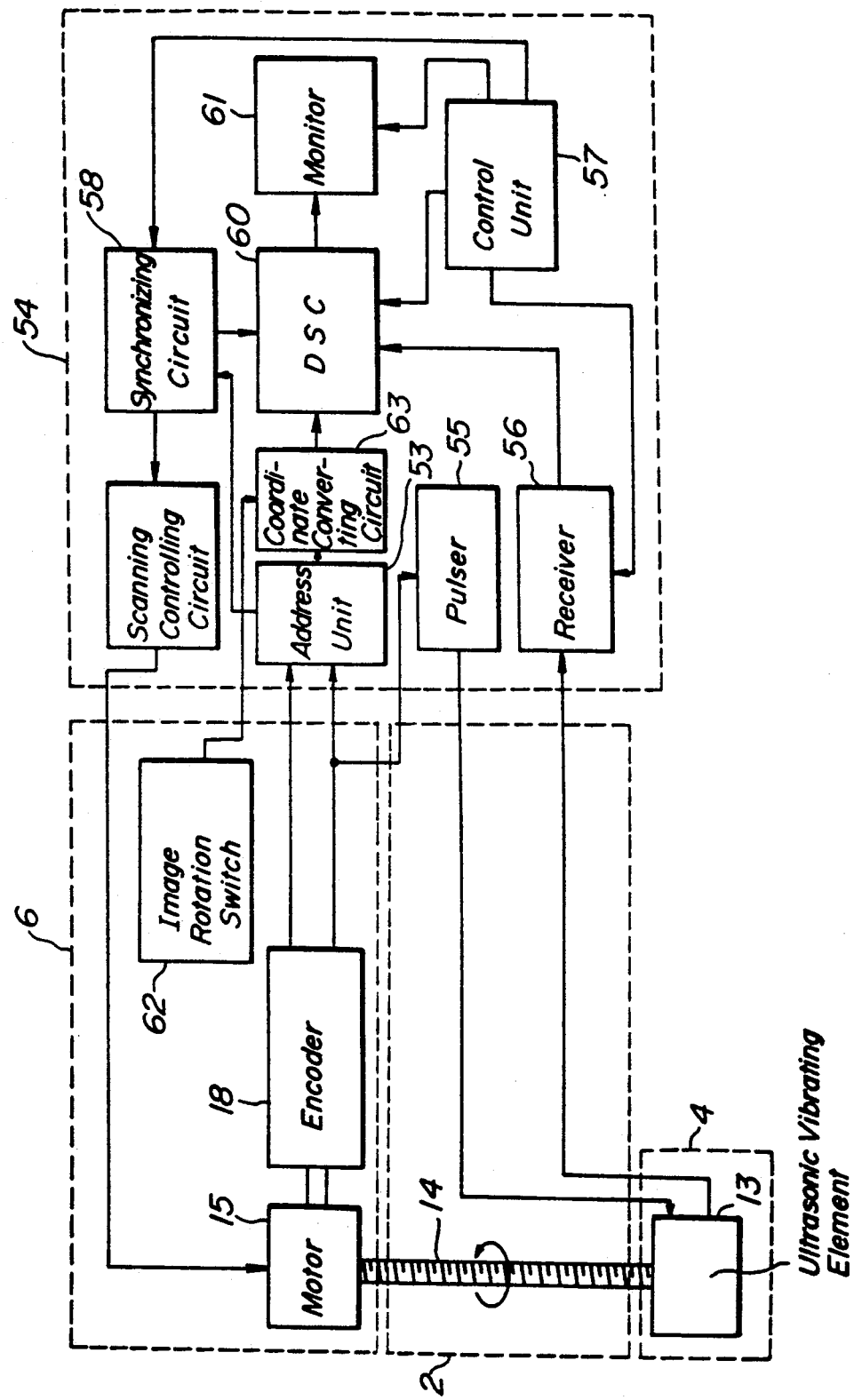
FIG. 15 is a block diagram of the sixth embodiment of the invention.

FIG. 15 is a block diagram depicting the sixth embodiment of the ultrasonic endoscope apparatus according to the invention. In the present embodiment, portions similar to those of the fifth embodiment are denoted by the same reference numerals and the explanation therefore is omitted. In this embodiment, instead of the delay circuit 52 of the fifth embodiment, there is arranged a coordinates converting circuit 63 between the address unit 53 and the DSC 60. The coordinates converting circuit 63 is connected to the image rotation switch 62 which controls a rotation amount in the coordinates converting circuit 63. The coordinates of the address signal supplied from the address unit 53 is rotated in the coordinates converting circuit 63 under controlling of the image rotation switch 62 with reference to the optical image and the ultrasonic tomographic image by an rotation amount represented by the following formula:

$$\begin{pmatrix} X \\ Y \end{pmatrix} = \begin{pmatrix} \cos\theta & 0 \\ 0 & \sin\theta \end{pmatrix} \begin{pmatrix} x \\ y \end{pmatrix}$$

The coordinate signal converted by the coordinates converting circuit 63 is supplied to the DSC 60. The DSC 60 generates a video signal under the controlling of the control unit 57 and the ultrasonic tomographic image rotated by the rotational amount calculated by the above formula is displayed on the monitor 61.

Figure 16:
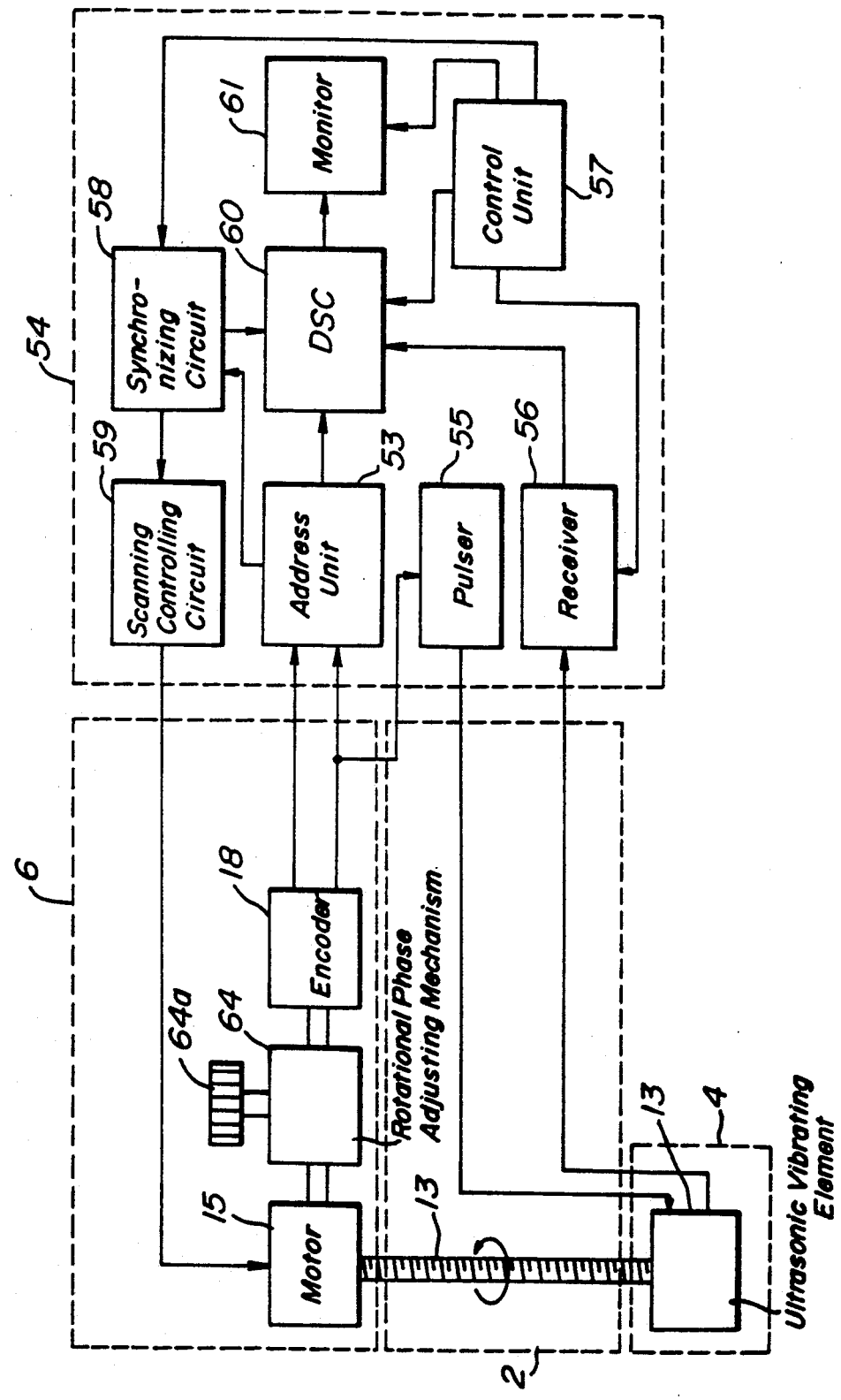
FIG. 16 is a block diagram of the seventh embodiment of the invention.

FIG. 16 is a block diagram representing the ultrasonic endoscope diagnostic apparatus according to the seventh embodiment of the invention. In this embodiment, instead of the delay circuit 52 and the coordinates converting circuit 63, there is provided a rotational phase adjusting mechanism 64 between the motor 15 and the encoder 18 to adjust the rotational phase of the ultrasonic vibrating element 13 in a mechanical manner. The adjusting amount is controlled by operating a knob 64a connected to the rotational phase adjusting mechanism 64 with reference to the optical image and the ultrasonic tomographic image. In this embodiment, it is possible to adjust the rotational phase of the encoder 18 so as to correspond to the rotational phase of the ultrasonic vibrating element 13, so that the deviation between the ultrasonic tomographic image and optical image due to the twist of the flexible shaft 14 can be corrected.

Figure 17:
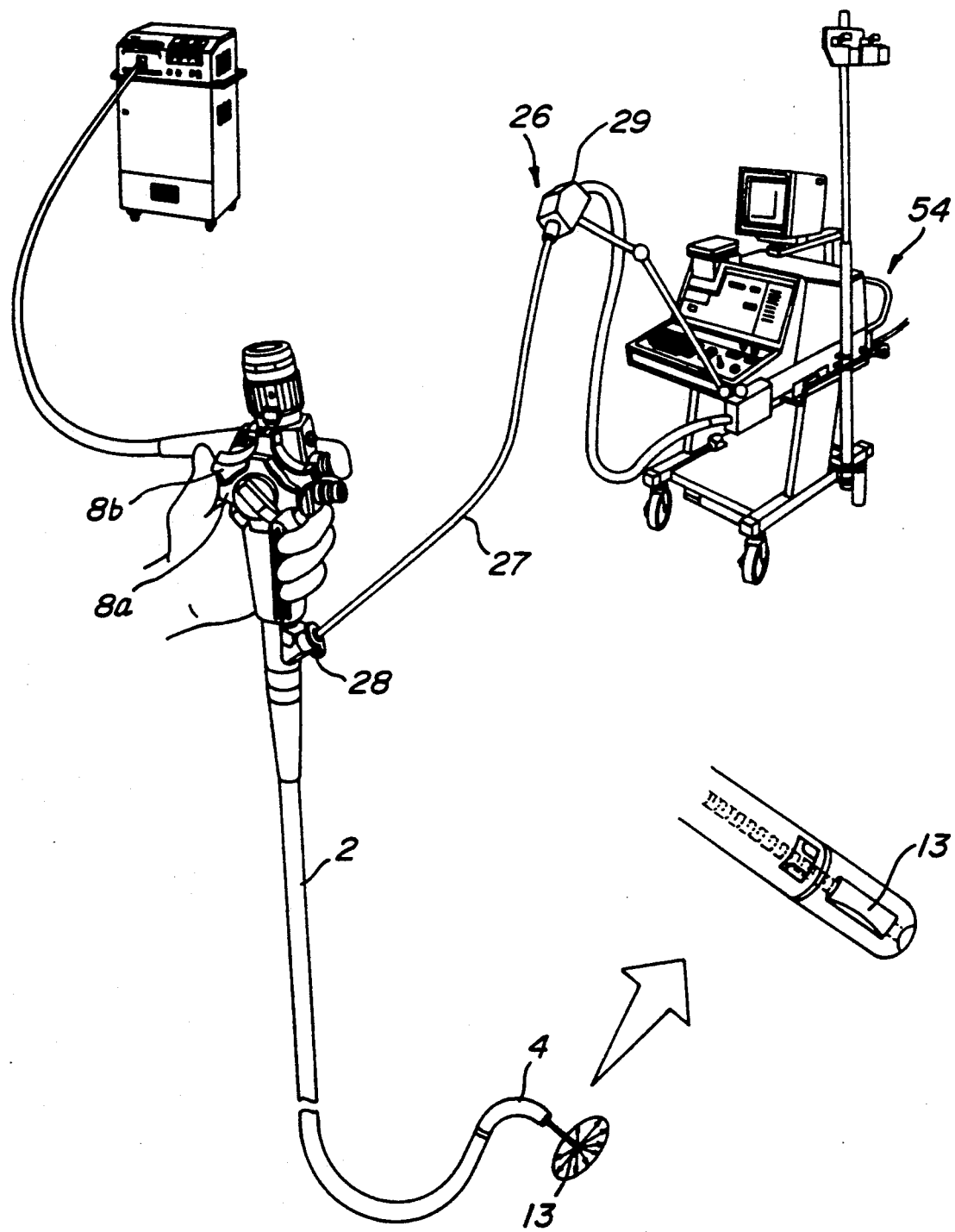
FIG. 17 is a schematic view illustrating a whole structure of the apparatus having a miniature ultrasonic probe.
Figure 18:
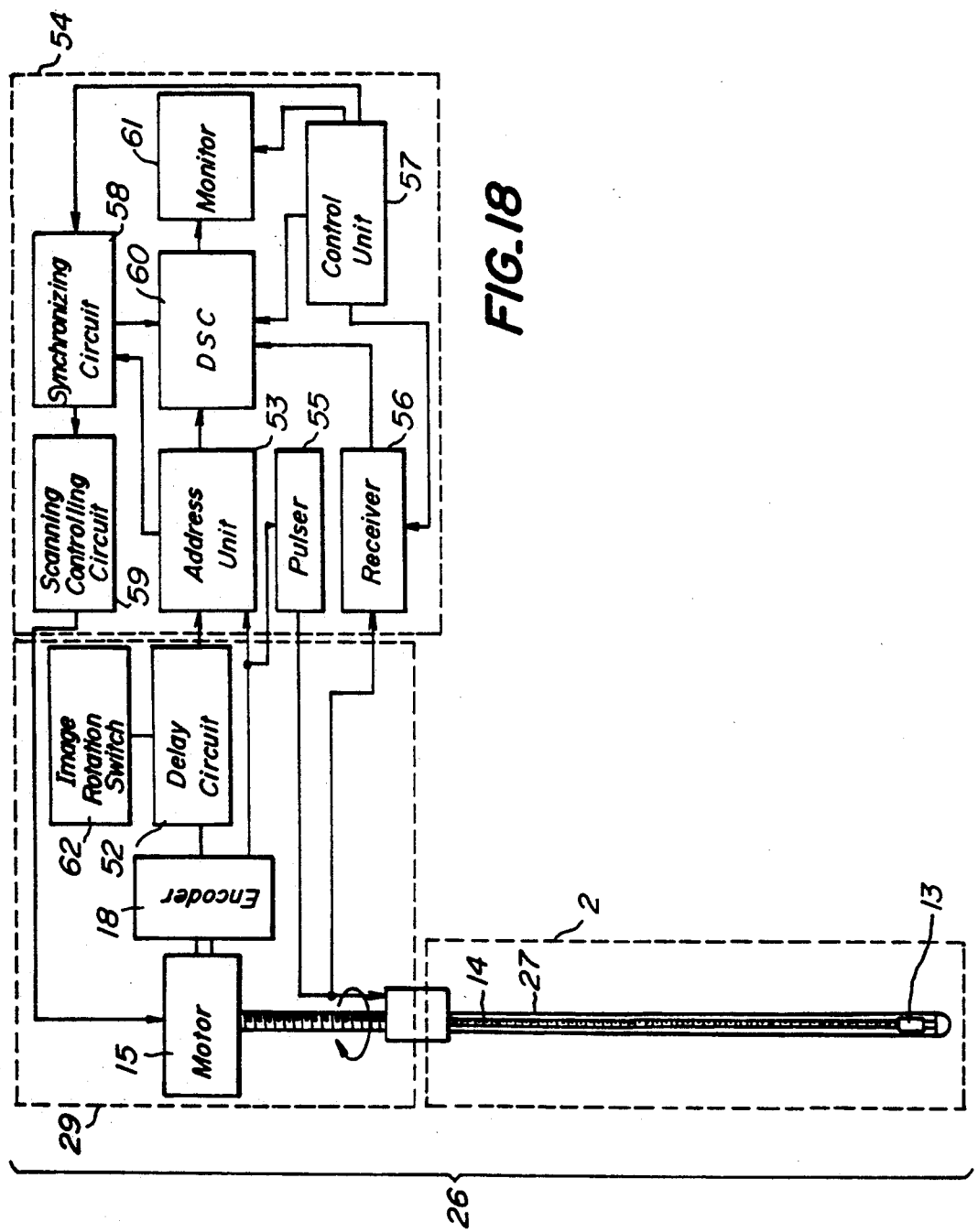
FIG. 18 is a block diagram of the eighth embodiment of the invention.

FIG. 17 is a schematic view representing an overall structure of the ultrasonic endoscope diagnostic apparatus having a miniature ultrasonic probe. The detailed structure of the apparatus is the same as the apparatus shown in FIG. 7. In this apparatus, there is a problem that the rotational phase of the motor 15 provided in the operating section 29 of the ultrasonic probe 26 may deviated from the actual rotational phase of the ultrasonic vibrating element 13 due to the twist of the flexible shaft 14 of the apparatus. FIG. 18 is a block diagram of the apparatus having the miniature ultrasonic probe shown in FIG. 17. The apparatus of this embodiment has the same circuit construction as that of the fifth embodiment explained above, and it is possible to compensate for the deviation of the relationship between the optical image and the ultrasonic tomographic image in entirely the same manner as that of the fifth embodiment.

In the above embodiments, the compensation for the deviation between the rotational phase of the motor 15 and the actual rotational phase of the ultrasonic vibrating element 13 is effected in a manual mode. In the embodiments in the following, the deviation is compensated for automatically.

Figure 19:
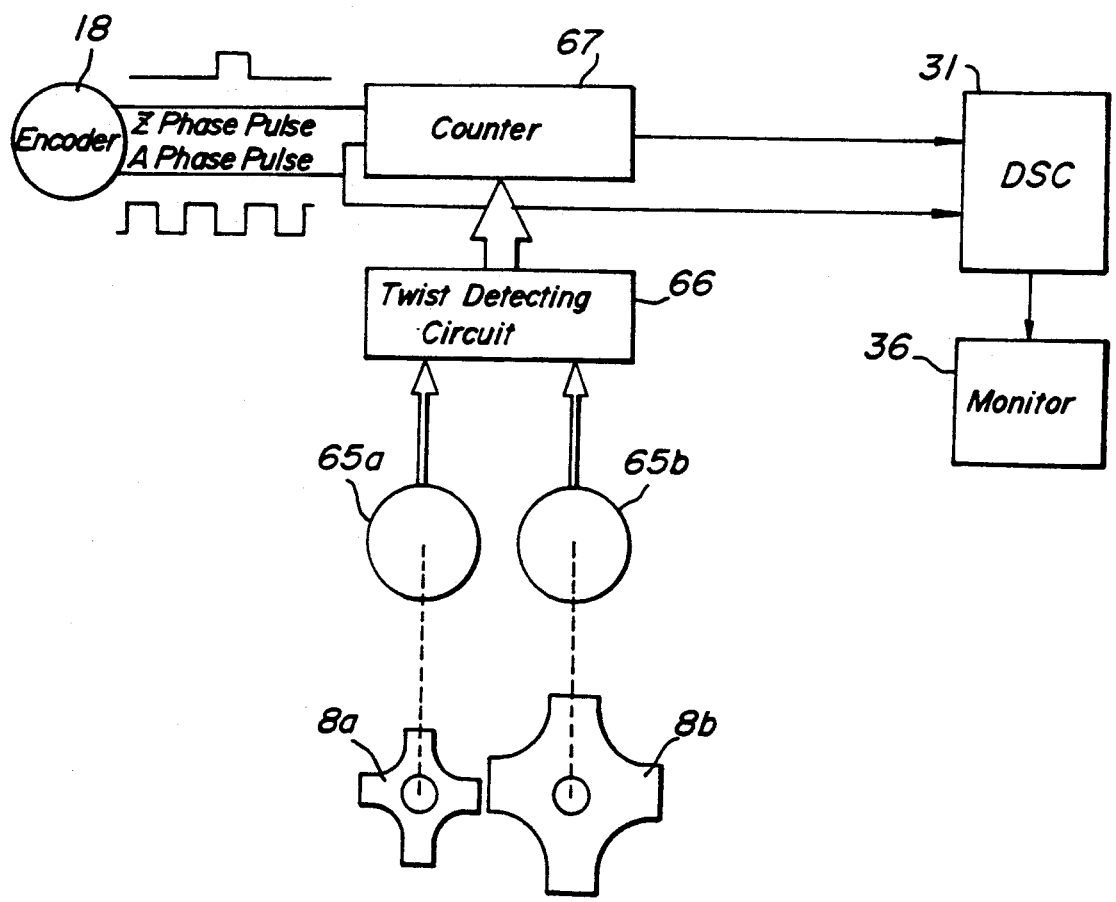
FIG. 19 is a block diagram of the ninth embodiment of the invention.

FIG. 19 is a block diagram showing the ultrasonic endoscope diagnostic apparatus according to the eighth embodiment of the invention. In this embodiment, to the angle knobs 8a, 8b for bending the bending section 3 of the insertion section 2 in the up/down and right-/left directions, are arranged encoders 65a, 65b in a coaxial manner, respectively, to detect the bending amount of the bending section 3. The bending amount of the bending section 3 detected by the encoders 65a, 65b are supplied to a twist detecting circuit 66 for detecting an amount and a direction of twist of the flexible shaft 14. In the twist detecting circuit 66, a twist amount and direction of the flexible shaft 14 are experimentally detected from the bending amount detected by the encoders 65a and 65b. The twist detecting circuit 66 includes a circuit for producing a preset count which is larger or smaller than a predetermined standard preset count corresponding to 0 (zero) twist. The preset count value produced in the circuit 66 is supplied to the counter 67. To the counter 67 are supplied the Z phase pulse and the A phase pulses from the encoder 18 which is connected to the proximal end portion of the flexible shaft 14 in order to detect the rotation of the ultrasonic vibrating element 13. In response to the Z phase pulse supplied from the encoder 18, the counter 67 counts the A phase timing pulses which are supplied from the encoder 18. When the count value reaches the preset count, the counter 67 generates a display start signal. The same as in the first embodiment, the display start signal is supplied to the DSC 31, and then the DSC 31 starts to supply the video signal to the monitor 36. In this manner, the ultrasonic tomographic image can be rotated on the monitor 36 in an opposite direction to the twist of the flexible shaft 14, so that the deviation between the ultrasonic tomographic image and the optical image is automatically compensated for on the monitor screen.

Figure 20:
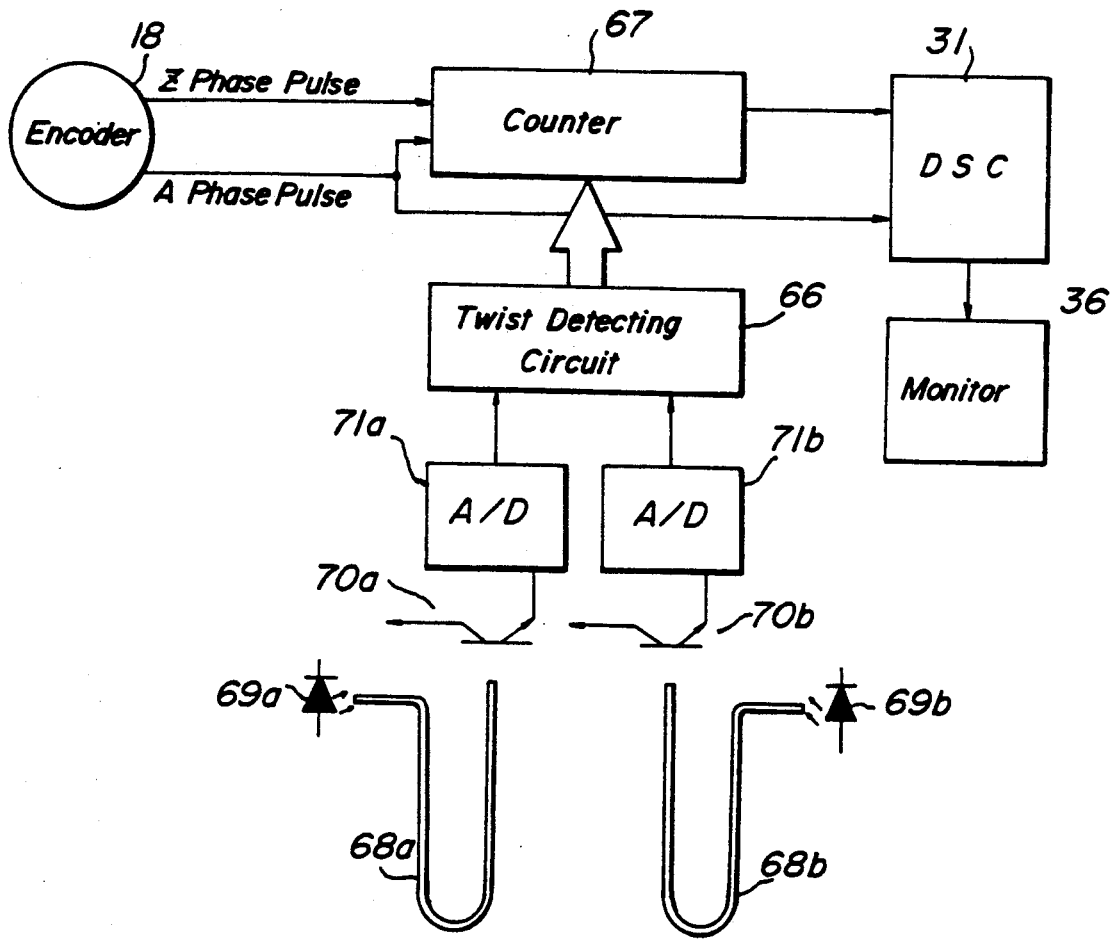
FIG. 20 is a block diagram of the tenth embodiment of the invention.

FIG. 20 is a block diagram depicting the ultrasonic endoscope diagnostic apparatus according to the ninth embodiment of the invention. In this embodiment, optical fibers 68a, 68b are inserted in the insertion section so as to be folded at the distal end portion of the insertion section 2 in order to detect the twist amount of the flexible shaft 14. The optical fiber 68a is to detect the bending amount of the flexible shaft in the UP/DOWN direction, and the optical fiber 68b in RIGHT/LEFT direction. At both one ends of the optical fibers 68a, 68b, there are provided light emitting diodes 69a and 69b, respectively, as light sources and at both the other ends of the fibers 68a, 68b, provided photo-transistors 70a, 70b, respectively, to detect the light intensity emanating from the other ends of the optical fibers 68a, 68b.

Figure 21:
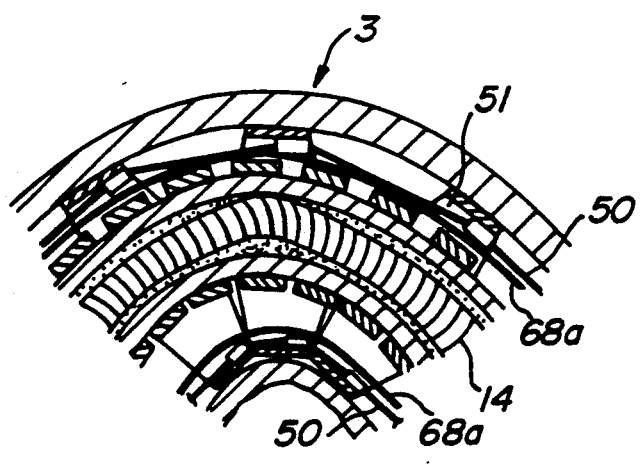
FIG. 21 is a cross sectional view representing an inside of the bending section according to the ninth embodiment of the invention.

The light intensities detected by the photo-transistors 70a, 70b are supplied to A/D converters 71a, 71b to produce digital signals. Since the intensities of light from the light emitting diodes 69a, 69b are decreased when the lights are transmitted in the fibers 68a, 68b, in accordance with the bending amount of the flexible shaft 14. In the twist detecting circuit 66, to which digital signals are supplied from the A/D converters 71a and 71b, it is possible to experimentally detect the twist amount of the flexible shaft by means of the digital signals. The same as in the eighth embodiment, the preset count corresponding to the twist amount of the flexible shaft 14 is supplied to the counter 67, and the Z phase pulse is delayed in the counter 67. According to the structure of this embodiment, it is possible to detect not only the twist of the flexible shaft 14 caused by the bending of the bending section 3 by operating the angle knobs 8a and 8b but also the twist of the flexible shaft 14 naturally caused when the insertion section 2 is inserted into the cavity. Therefore, compensation for the deviation between the ultrasonic tomographic image and the optical image can be effected more precisely. FIG. 21 is a cross sectional view illustrating a part of the bending section 3 of the insertion section 2 in which the optical fiber 68a is arranged. The optical fiber 69a is arranged in a plane which is perpendicular to the plane of the optical fiber 68a.

Figure 22:
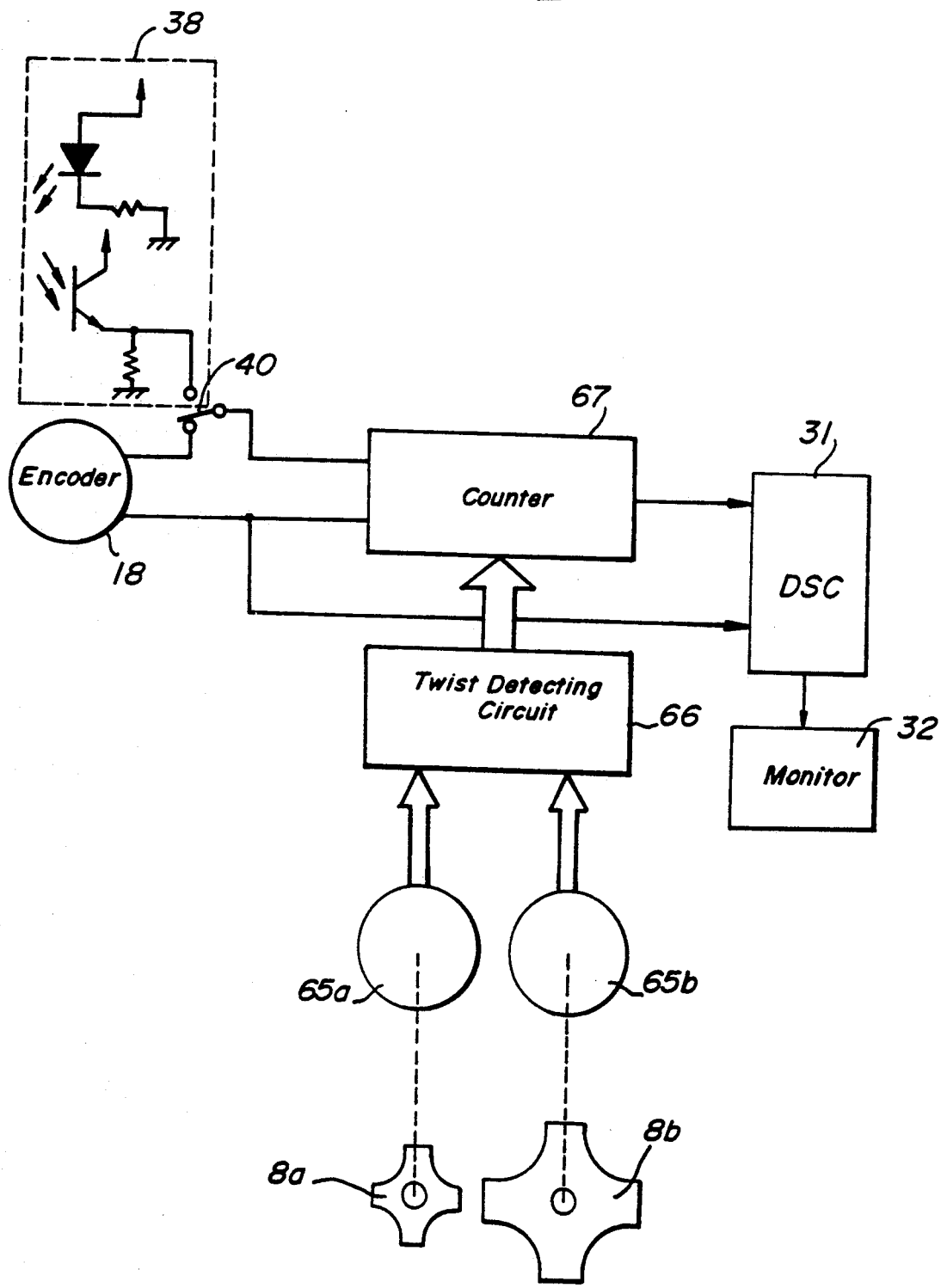
FIG. 22 is a block diagram showing the construction of the tenth embodiment of the invention.

The structure according to the ninth embodiment described above can be applied to the ultrasonic endoscope apparatus having a miniature ultrasonic probe. In this case, the structures of the channel 28 and the insertion tube 27 shown in FIGS. 8A, 8B, 9A, 9B and 10 may be used for detecting the standard rotational position of the ultrasonic vibrating element 13. FIG. 22 is a block diagram representing the tenth embodiment of the invention. In this embodiment, the structure shown in FIG. 10 is applied to the apparatus. That is to say, the mark 39 is provided on the outer surface of the flexible shaft 14 and the rotation of the flexible shaft 14 is detected by detecting the mark 39 by mean of the photo-detector 38. The twist amount and direction of the flexible shaft is detected by detecting the rotational amount and direction of the angle knobs 8a, 8b by means of the encoders 65a, 65b the same as in the previous embodiment.

The present invention is not limited to the above embodiments and various changes and modifications in form and details may be made without departing from the scope and spirit of the invention. For example, the image rotation switch in FIG. 13, etc. may be provided not in the sub-operating section 6 but in the ultrasonic observation section 54. And an indicator, e.g. LED, may be provided on the sub-operating section 6 such that the indicator indicates that the image rotation switch is in an operating mode, so that the operator can know that the image rotation switch has been operated to correct the deviation of the rotational relationship between the ultrasonic tomographic image and the optical image.

What is claimed is:

1. An ultrasonic diagnostic apparatus for observing an ultrasonic tomographic image of a bodily portion of a patient,:
    an insertion section which is insertable into a cavity of the body of the patient and having a distal end and a proximal end;
    an optical observation means for observing an optical image of said bodily portion of the patient, said optical means including an objective lens system arranged at the distal end of the insertion section and defining an observation field;
    an ultrasonic observation means for observing an ultrasonic tomographic image of said bodily portion of the patient and having an ultrasonic vibrating element arranged within the distal end of the insertion section;
    a display means electrically coupled with said ultrasonic vibrating element and having a display screen for displaying the ultrasonic tomographic image of said bodily portion of the patient;
    means for obtaining a direction indicator representing a predetermined positional relationship between the ultrasonic tomographic image and the optical image; and
    a display controlling means for displaying said direction indicator in a superposed manner with the ultrasonic tomographic image displayed on the display screen of the displaying means.

2. An apparatus as claimed in claim 1, wherein said display means comprises means for displaying the ultrasonic tomographic image in the radial scanning mode, and said display controlling means comprises an image rotating means for rotating the orientation of the ultrasonic tomographic image and the direction indicator on the display screen in conjunction with each other by the same rotation angle.

3. An apparatus as claimed in claim 2, wherein said ultrasonic observation means comprises a means for supporting the ultrasonic vibrating element rotatably about an axis which is parallel to a longitudinal axis of the distal end of the insertion section, a flexible shaft arranged to extend within the insertion section and having a distal end coupled with the ultrasonic vibrating element and a proximal end, and a driving means coupled with the proximal end of the flexible shaft for rotating the ultrasonic vibrating element via the flexible shaft.

4. An apparatus as claimed in claim 3, wherein said ultrasonic vibrating element is arranged rotatably in the distal end of the insertion section such that the ultrasonic tomographic image is perpendicular to a longitudinal axial direction of the distal end of the insertion section, and said objective lens system of the optical observation means is arranged in a side wall of the distal end of the insertion section, whereby said direction indicator represents the observation direction of the optical observation means with respect to the ultrasonic tomographic image.

5. An apparatus as claimed in claim 3, wherein said ultrasonic vibrating element is arranged rotatably in the distal end of the insertion section such that the ultrasonic tomographic image is perpendicular to a longitudinal axial direction of the distal end of the insertion section, and said objective lens system of the optical observation means is arranged in a front end wall of the distal end of the insertion section, whereby said direction indicator represents a direction of a line connecting the center axis of the rotation of the ultrasonic vibrating element to an optical axis of the optical observation means.

6. An apparatus as claimed in claim 3 wherein said display control means comprises an encoder arranged in the driving means for detecting a rotational position of the ultrasonic vibrating element to produce timing pulses which represent an amount of the rotation and an origin signal which represent a predetermined origin of the rotational movement of the ultrasonic vibrating element, a count presetting circuit for generating a preset count value which corresponds to the rotational angle of the ultrasonic image, a rotation angle changing circuit having a counter which receives the preset count value and starts to count the timing pulses supplied from the encoder in response to the origin signal to produce a display start signal when a count value becomes equal to the preset count value, and an indicator generator which generates an image signal of the direction indicator in response to the origin signal, and said displaying means comprises a digital scan converter which receives the timing pulses and display start signal supplied from the rotation angle changing circuit, an electric echo signal supplied from the ultrasonic vibrating element, and the image signal of the direction indicator.

7. An ultrasonic diagnostic apparatus for observing an ultrasonic tomographic image of a bodily portion of a patient,:
  an insertion section which is insertable into a cavity of the body of the patient and having a distal end and a proximal end;
  an optical observation means for observing an optical image of said bodily portion of the patient, said optical means including an objective lens system arranged at the distal end of the insertion section and defining an observation field;
  an ultrasonic observation means for observing an ultrasonic tomographic image of said bodily portion of the patient and having an ultrasonic vibrating element arranged within the distal end of the insertion section;
  a display means electrically coupled with said ultrasonic vibrating element for receiving an echo signal generated from the ultrasonic vibrating element and including a display screen for displaying the ultrasonic tomographic image of said bodily portion of the patient; and
  a display controlling means for rotating the ultrasonic tomographic image displayed on the display screen of the displaying means to compensate any deviation between the ultrasonic tomographic image and the optical image.

8. An apparatus as claimed in claim 7, wherein said ultrasonic observation means comprises a means for supporting the ultrasonic vibrating element rotatably about an axis which is parallel to a longitudinal axis of the distal end of the insertion section, a flexible shaft arranged within the insertion section and having a distal end coupled with the ultrasonic vibrating element and a proximal end, and a driving means coupled with the proximal end of the flexible shaft for rotating the ultrasonic vibrating element via the flexible shaft.

9. An apparatus as claimed in claim 8, wherein said displaying means comprises a rotational position detecting device arranged at the distal end of the insertion section for detecting the rotational position of the ultrasonic vibrating element with respect to the insertion section to produce a rotational position indicating signal, and a digital scan converter for receiving the echo signal and the rotational position indicating signal to generate a video signal, said video signal being formed such that the ultrasonic tomographic image is displayed on the display screen in a predetermined rotational direction with respect to the optical image.

10. An apparatus as claimed in claim 9, wherein said rotational position detecting device is constructed such that said rotational position indicating signal includes a first phase signal which is generated once in one rotation of the ultrasonic vibrating element and a second phase signal which is produced each time the ultrasonic vibrating element is rotated by a predetermined angle.

11. An apparatus as claimed in claim 10, wherein said display controlling means comprises a delay circuit which delays or advances the first phase signal and an image rotation switch which controls the delay circuit.

12. An apparatus as claimed in claim 10, wherein said display controlling means comprises an image rotation switch which is manually operated to generate a rotation signal, and a coordinate converting circuit which converts the coordinate of the video signal in accordance with the rotation signal.

13. An apparatus as claimed in claim 11 or 12, wherein said image rotation switch is arranged on the proximal end of the insertion section.

14. An ultrasonic diagnostic apparatus for observing an ultrasonic tomographic image of a bodily portion of a patient, comprising:
  an insertion section which is insertable into a cavity of the body of the patient and having a distal end and a proximal end and a bending section arranged near the distal end;
  an ultrasonic observation means for observing an ultrasonic tomographic image of said bodily portion of the patient and having an ultrasonic vibrating element arranged within the distal end of the insertion section;
  a display means electrically coupled with said ultrasonic vibrating element for receiving an echo signal supplied form the ultrasonic vibrating element to produce a video signal and including a display screen for displaying the ultrasonic tomographic image of said bodily portion of the patient;
  a twist detecting means for detecting one of (i) an amount of and (ii) an amount and a direction of the bending moment of the bending section of the insertion section to produce a twist detection signal; and
  a display controlling means for receiving the twist detection signal and rotating the ultrasonic tomographic image displayed on the display screen of the displaying means in accordance with the twist detection signal.

15. An apparatus as claimed in claim 14, wherein said display controlling means comprises a delay circuit which delays an origin signal of the video signal in accordance with the twist detection signal.

16. An apparatus as claimed in claim 14, wherein said twist detecting means comprises detectors for detecting rotation angles of angle knobs arranged at the proximal end of the insertion section for adjusting the bending movement of the bending section.

17. An apparatus as claimed in claim 14, wherein said twist detecting means comprises a device for detecting a bending movement of the bending section.

18. An apparatus as claimed in claim 17, wherein said device for detecting the bending movement of the bending section comprises optical fibers arranged within the insertion section, light sources for projecting light into incident ends of the optical fibers, light receiving elements for receiving light transmitted through the optical fibers and emanating from exit ends thereof, and a circuit for detecting the twisting movement of the bending section in accordance with an intensity of the light transmitted through the optical fibers.

* * * * *